United States Patent
Pasricha et al.

(10) Patent No.: US 7,541,156 B1
(45) Date of Patent: Jun. 2, 2009

(54) METHOD OF IDENTIFYING ANTINOCICEPTIVE COMPOUNDS USING PROTEASE ACTIVATED RECEPTOR-2

(76) Inventors: Pankaj J. Pasricha, 3315 Oak Links Ave., Houston, TX (US) 77059; Willemijntje A. Hoogerwerf, 4400 Avenue N #38, Galveston, TX (US) 77550; John Winston, 2605 Ryder Ct., League City, TX (US) 77573; Maria-Adelaide Micci, 2880 Morning Pond La., Dickinson, TX (US) 77539; Helen Hellmich, 6 Cadena Ct., Galveston, TX (US) 77554; Mohan Shenoy, 3222 69th St., Apt. 133, Galveston, TX (US) 77551

( * ) Notice: Subject to any disclaimer, the term of this patent is extended or adjusted under 35 U.S.C. 154(b) by 226 days.

(21) Appl. No.: 11/108,173

(22) Filed: Apr. 18, 2005

Related U.S. Application Data

(63) Continuation of application No. 09/794,465, filed on Feb. 27, 2001, now abandoned.

(60) Provisional application No. 60/186,237, filed on Mar. 1, 2000.

(51) Int. Cl.
*G01N 33/53* (2006.01)
*G01N 33/567* (2006.01)

(52) U.S. Cl. ........................................ 435/7.2

(58) Field of Classification Search .............. None
See application file for complete search history.

(56) References Cited

U.S. PATENT DOCUMENTS

| 5,888,529 | A | * | 3/1999 | Bunnett et al. | 424/422 |
|---|---|---|---|---|---|
| 6,077,990 | A | | 6/2000 | Leung et al. | |
| 6,630,451 | B1 | | 10/2003 | Zhang et al. | |

OTHER PUBLICATIONS

Nystedt S et al. Proc. Natl. Acad. Sci. 91:9208-9212, 1994.*
Nystedt S et al. Eur. J. Biochem. 232:84-89, 1995.*
CorveraCU, et al. J. Clin. Invest. 100(6):1383-1393, 1997.*
Nystedt S, et al. Eur. J. Biochem. 232:84-89, 1995.*
Steinhoff et al., Nature Medicine 6(2):151-58(2000).
Dery et al., Am. J. Physiol. 274:C1429-1452(1998).

* cited by examiner

*Primary Examiner*—Robert Landsman
(74) *Attorney, Agent, or Firm*—Benjamin Aaron Adler

(57) ABSTRACT

The invention provides a method of decreasing pain in a subject, the method comprising administering to the subject an amount of a compound effective to decrease activation of protease activated receptor-2.

2 Claims, 6 Drawing Sheets

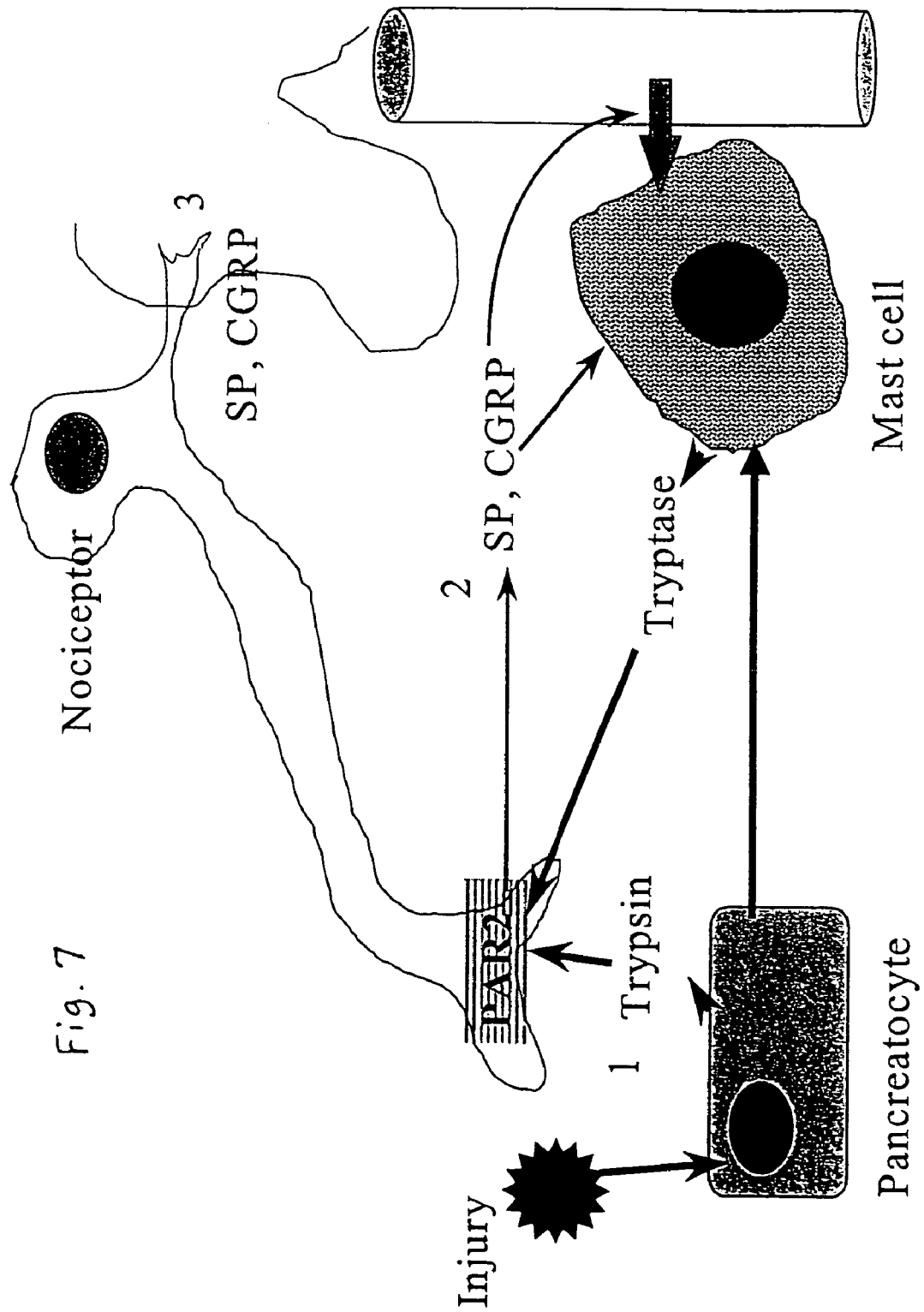

METHOD OF IDENTIFYING ANTINOCICEPTIVE COMPOUNDS USING PROTEASE ACTIVATED RECEPTOR-2

This application is a continuation of U.S. patent application Ser. No. 09/794,465 file Feb. 27, 2001 (abandoned), which claims priority of U.S. Provisional Patent Application No. 60/186,237, filed Mar. 1, 2000 (abandoned). These applications are hereby incorporated by reference.

FIELD OF THE INVENTION

The subject invention is directed generally to a method for decreasing pain, and more particularly to decreasing activation of protease activated receptor-2 which is involved in nociception in painful inflammatory diseases.

BACKGROUND OF THE INVENTION

Throughout this application various publications are referenced, many in parenthesis. The disclosures of each of these publications in their entireties are hereby incorporated by reference in this application.

The proteinase-activated receptors (PAR) are a family of four G-protein coupled receptors (Vu et al. 1991; Nystedt et al. 1994; Nystedt et al. 1995; Ishihara et al. 1997; Xu et al. 1998; Kahn et al. 1998) that share a unique mechanism of activation. Serine proteases such as trypsin and thrombin cleave PARs, unmasking an extracellular N-terminal domain that subsequently binds and activates the receptor, thus acting as a tethered ligand. Synthetic activating peptides that correspond to the tethered ligands of the various PARs can also activate their individual receptor directly (Al-Ani et al. 1999; Hollenberg et al. 1997).

The first PAR discovered was the thrombin receptor (protease activated receptor-1; PAR-1) from human platelet progenitor cells. The serine protease α-thrombin cleaves the extracellular, N-terminal peptide chain of PAR-1 between Arg-41 and Ser-42 to expose a truncated N terminus bearing the peptide recognition motif SEQ ID NO:5: SFLLRN. Synthetic peptides containing this epitope have full PAR-1 agonist properties independent of thrombin activation, confirming that the receptor-linked peptide sequence serves as an activating ligand. Notably, PAR-1 mediates most of the cellular actions of thrombin, including platelet aggregation, cell proliferation, inflammatory responses, and neurodegeneration.

Researchers have identified three more members of this class of G protein-coupled receptors, PAR-2, PAR-3, and PAR-4, which also are activated by a serine protease to initiate an intramolecular ligand-activation mechanism.

Nystedt et al. (1995) described the receptor they designated proteinase activated receptor-2 (PAR-2) as a member of the large family of 7-transmembrane-region receptors that couple to guanosine-nucleotide-binding proteins. Proteolytic cleavage of PAR-2's extracellular amino terminus leaves the new amino terminus, a tethered ligand, free to interact with another region of the receptor to effect receptor activation. Nystedt et al. (1995) noted that PAR2 shares this special mode of activation with the thrombin receptor, for which this mechanism was first described (see above).

Nystedt et al. (1994) cloned the mouse Par2 sequence from genomic DNA. When expressed in frog oocytes, the receptor could be activated with nanomolar concentrations of the serine protease trypsin but not with thrombin in doses up to 100 nM. It was judged that the gene was present in the genome in a single copy. Two protein-encoding exons were identified separated by 10 kb.

Nystedt et al. (1995) cloned the human gene. The deduced protein sequence was similar to that of the mouse Par2 receptor and, when expressed in Chinese hamster ovary cells, the human PAR2 responded to trypsin and a peptide from the receptor sequence. Northern blot analysis of receptor expression showed that the receptor transcript is widely expressed in human tissues with especially high levels in pancreas, liver, kidney, small intestine, and colon. Moderate expression was detected in many organs, but none in brain or skeletal muscle. By fluorescence in situ hybridization, the gene was mapped to 5q13. Nystedt et al. (1995) noted that the location of the thrombin receptor gene (F2R), also mapped to 5q13, which raised questions concerning the evolution of proteinase activated receptors.

The general structure of proteinase activated receptors is shown in FIG. 6. Referring to FIG. 6, the receptor (12) includes an amino terminus (18). Within the amino terminus (18) of the receptor (12) is a portion (20) which is a peptide agonist for the receptor. When the receptor is exposed to it's appropriate cleavage agent, the cleavage agent cleaves the most amino terminal part of the molecule (22) leaving the portion which is a peptide agonist (20) exposed. The peptide agonist (20) reacts with the binding site (24) for the peptide agonist (which is a part of the remainder of the receptor molecule) and binds thereto, activating the receptor. The site between the amino acid residues of the peptide agonist (20) and the most amino terminal part of the molecule (22) is the cleavage site (26).

The amino acid sequence of human PAR-2 is provided at GenBank Accession No. P55085. The receptor consists of 397 amino acids, of which 1-25 represent a signal peptide. Amino acids 26-36 represent a propeptide which is removed for receptor activation. Trypsin cleaves the receptor at SKGR ↓ SLIG (the cleavage site; amino acids 33-40), leaving a peptide agonist (tethered ligand) having the amino acid sequence SEQ ID NO:6: SLIGKV-NH$_2$ (amino acids 37-42). The residues of this peptide agonist interact with extracellular domains of the cleaved receptor, resulting in activation of the receptor. Steinhoff et al. (2000), Lerner et al. (1996), Kawabata et al. (1999), Andrade-Gordon et al. (1999), Bohm et al. (1996), Kahn et al. (1996), Dery et al. (1998), Nystedt et al. 1996, U.S. Pat. No. 6,017,890 (issued Jan. 25, 2000), PCT International Publication No. WO 99/42475 (published Aug. 26, 1999), and PCT International Publication No. WO 98/34948 (published Feb. 5, 1998), discuss protease activated receptors further, including the design of agonists and antagonists for these receptors, and are each incorporated herein by reference.

Recently, proteinase-activated receptor 2 (PAR-2) expression was detected on a subset of peripheral peptidergic neurons and was shown to be involved in the neurogenic component of inflammation (Steinhoff et al. 2000).

Inflammation and its sequelae are known to cause significant changes in the somatic sensory nervous system affecting peripheral nerves, spinal cord and supraspinal structures. Several biological agents induced by inflammation such as neurotrophins (e.g. nerve growth factor or NGF), prostanoids, bradykinin and various cytokines can sensitize peripheral nociceptors (Dray 1995). This leads to an increase in afferent signaling which in turn may cause sensitization at the central level, resulting in amplification and persistence of pain. Amongst the many potential sensitizing factors in this inflammatory soup, little attention has been paid to the role of proteases. These enzymes are derived from humoral (thrombin, factor Xa) and cellular (trypsin, tryptase and other tryptic enzymes from mast cells) sources (Cocks and Moffat 2000). In addition, inflammation in specific organs such as the pancreas may result in a significant release and activation of endogenous proteases (Hofbauer et al. 1998; Nguyen et al. 1999).

Pain associated with inflammation, or not, plaques many people. Any means for alleviating such pain would be useful.

SUMMARY OF THE INVENTION

The subject invention is based on the determination that the local release of activated proteases leads to neuronal sensitization via a PAR mediated mechanism and contributes to the pathogenesis of pain that often if not invariably accompanies inflammation. This is particularly true for organs such as the pancreas where inflammation results in massive activation of endogenous proteases such as trypsin. The results herein show that PAR-2 activation can sensitize adult rat DRG neurons in vitro. Further, activation of PAR-2 within the pancreas can also sensitize this organ to noxious stimulation in vivo. These findings show an important role for PAR-2 and proteases in nociception.

The subject invention provides a method which involves protease activated receptor-2 (PAR-2). More particularly, the invention provides a method of decreasing pain in a subject, the method comprising administering to the subject an amount of a compound effective to decrease activation of a neuronal protease activated receptor, such as protease activated receptor-2, in the subject. Such a method may be practiced in subjects having inflammatory conditions, or not having inflammatory conditions.

BRIEF DESCRIPTION OF THE DRAWINGS

These and other features and advantages of this invention will be evident from the following detailed description of preferred embodiments when read in conjunction with the accompanying drawings in which:

FIG. 7 shows the involvement of PAR-2 in nociceptive signaling in pancreatitis. 1: In pancreatitis, PAR-2 receptors on sensory neurons are activated by proteases released from injured pancreatic epithelial cells. Degranulation of mast cells releases tryptase that also acts on PAR-2 receptors. 2: PAR-2 stimulated release of CGRP and SP occurs peripherally, which further amplifies inflammation and mast cell degranulation. 3: Central release of these neurotransmitters leads to activation of nociceptive pathways and an increase in c-FOS expression. Peripheral sensitization of the VR-1 receptor also occurs, perhaps mediated by PAR-2 induced increases in intracellular calcium.

DETAILED DESCRIPTION OF THE INVENTION

Figure 1:
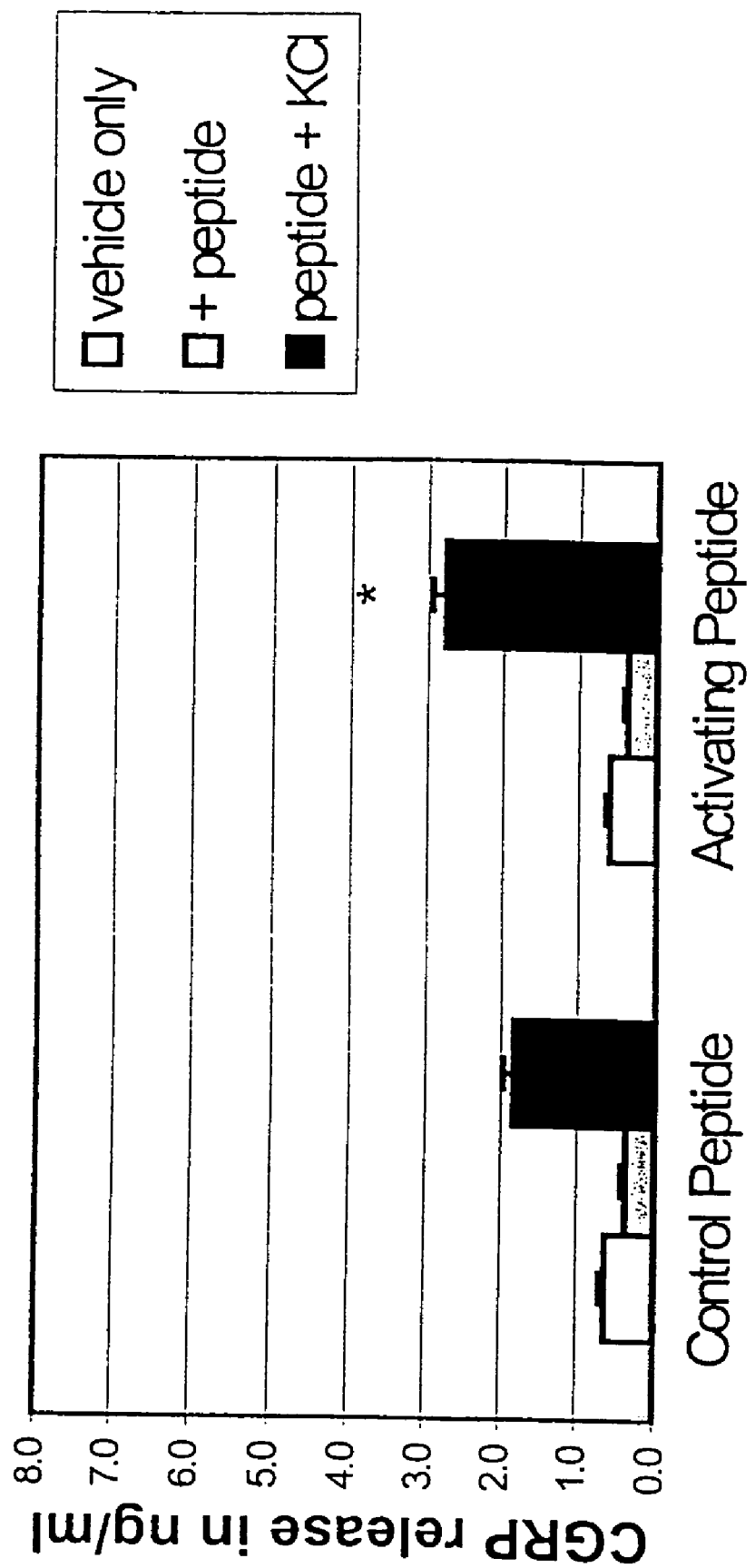
FIG. 1 is a histogram showing the amount of CGRP released from cultured adult rat thoracic DRG neurons during a 10 minute pretreatment with either AcPep (10 μM) or CoPep (10 μM). Cultures were then treated with KCl (70 mM) for 10 minutes in the presence of AcPep or CoPep. Data are represented as the mean release of wells (KCl=total 16 wells) from three separate experiments. Pre-treatment with AcPep (10 μM) increased CGRP release induced by KCl (70 mM), 2.7 ng/ml with AcPep vs 1.8 with CoPep (*p<0.001).
Figure 2:
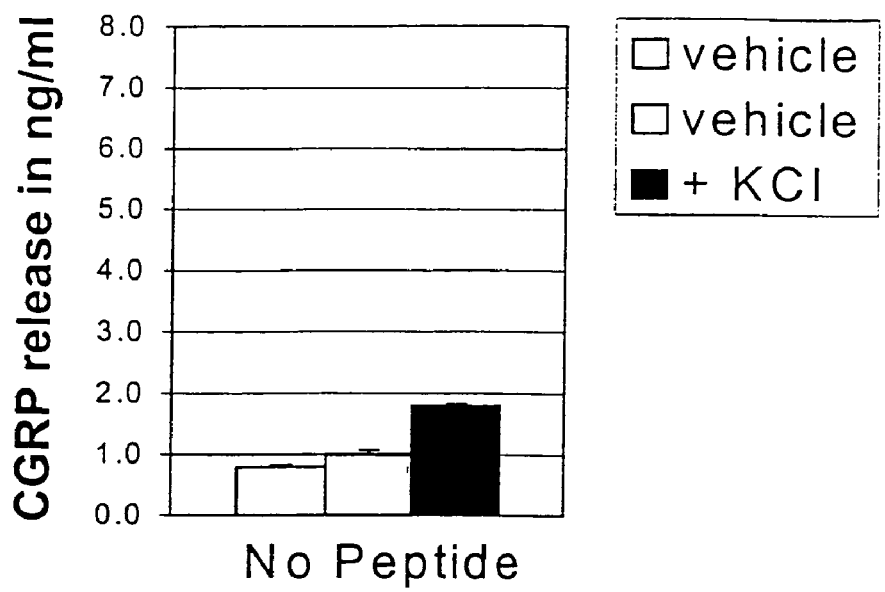
FIG. 2 is a histogram showing the amount of CGRP released from cultured adult rat thoracic DRG neurons.
Figure 4:
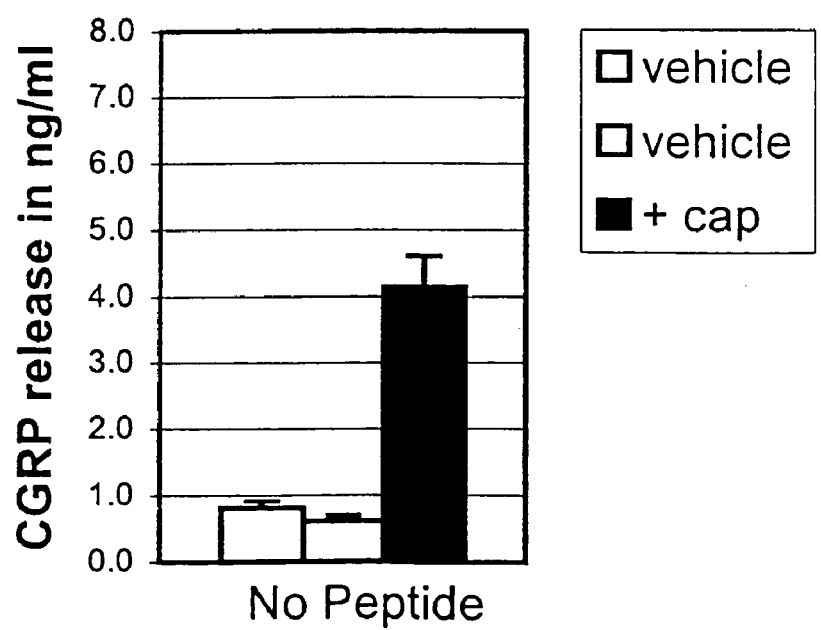
FIG. 4 is a histogram showing the amount of CGRP released from cultured adult rat thoracic DRG neurons.
Figure 3:
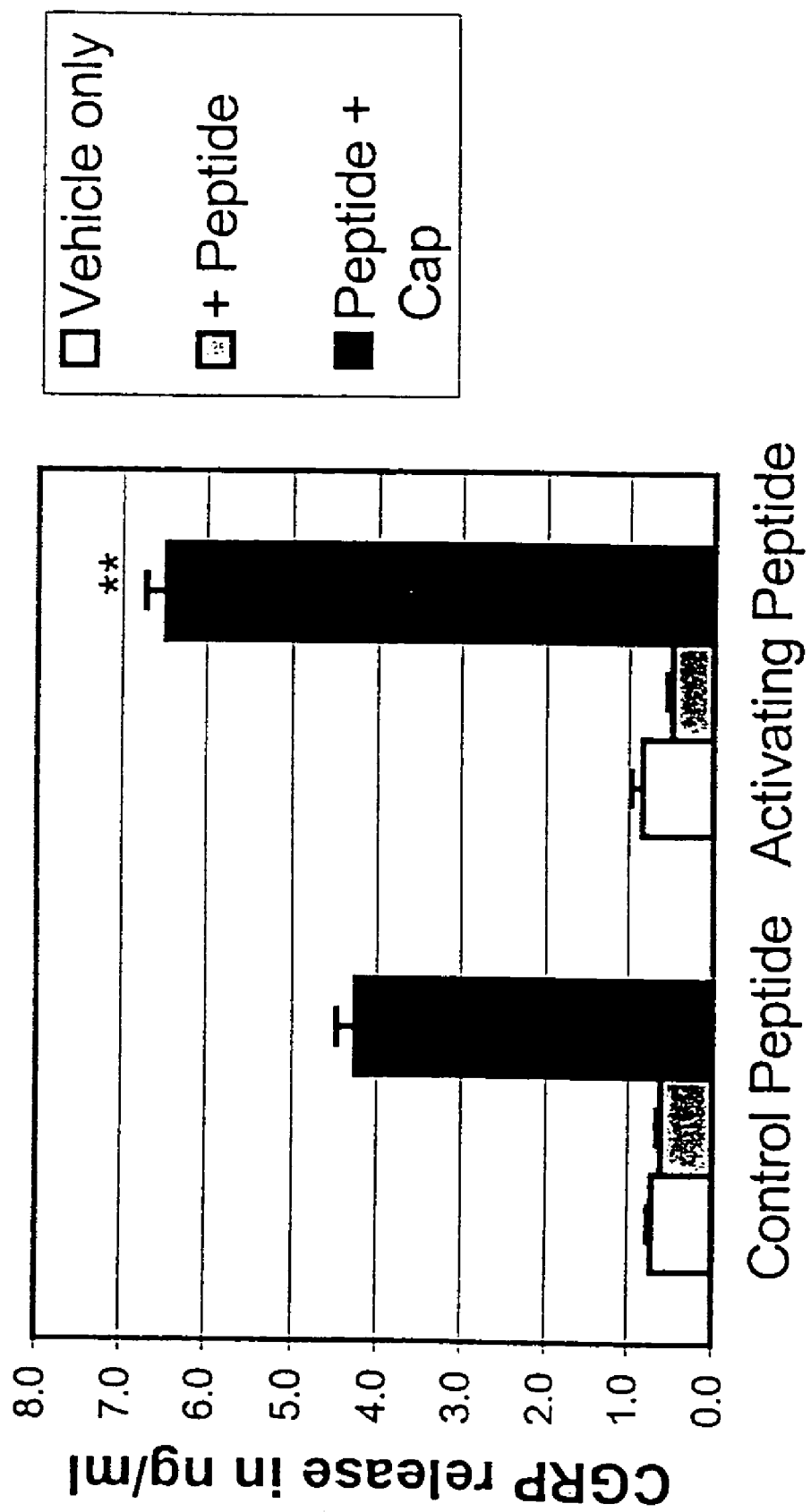
FIG. 3 is a histogram showing the amount of CGRP released from cultured adult rat thoracic DRG neurons during a 10 minute pretreatment with either AcPep (10 μM) or CoPep (10 μM). Cultures were then treated with Capsaicin (50 nM) for 10 minutes in the presence of AcPep or CoPep. Data are represented as the mean release of wells (Caps=total 18 wells) from three separate experiments. Pre-treatment with AcPep (10 μM) increased CGRP release induced by Capsaicin (50 nM), 7.3 ng/ml with AcPep vs 4.77 with CoPep (**p<0.01)

The subject invention is based on the discovery that decreasing activation of neuronal protease activated receptors, such as protease activated receptor-2 (PAR-2), in a subject can decrease pain in a subject. The invention thus provides a method of decreasing pain in a subject, the method comprising administering to the subject an amount of a compound effective to decrease activation of protease activated receptor-2. The decrease in activation of protease activated receptor-2 can comprise decreasing protease activated receptor-2 gene expression in cells of the subject. This can be accomplished by exposing the cells to a compound which decreases protease activated receptor-2 gene expression, such as an antisense oligonucleotide targeted to the protease activated receptor-2 gene. Decreasing activation of protease activated receptor-2 can also comprise exposing the cells to an inhibitor of the protease activated receptor-2, or by exposing the cells to a compound which interferes with transmembrane structure of the protease activated receptor-2.

The protease activated receptor-2 comprises an amino terminus, a peptide agonist, a binding site for the peptide agonist, and a cleavage site between the amino terminus and the peptide agonist. Decreased activation of PAR-2 can thus be accomplished by decreasing cleavage at the cleavage site (such as by blockage of the cleavage site or by removal of agents which cleave at the cleavage site), by blockage of the peptide agonist, by blockage of the binding site for the peptide agonist, by blockage of the three dimensional interaction between the peptide agonist and the binding site for the peptide agonist, by removal of the peptide agonist, by removal of the binding site for the peptide agonist, by removal of a portion of the protease activated receptor-2 such that the three dimensional interaction between the peptide agonist and the binding site for the peptide agonist is prevented, by preventing gene expression of the protease activated receptor-2, by preventing gene expression of the peptide agonist, by preventing gene expression of the binding site for the peptide agonist, or by preventing gene expression of the cleavage site.

It is also possible to interfere with the downstream effectors of the protease activated receptor. Effector systems include, for example, intracellular signaling pathways and second messenger pathways. Interference with the downstream effectors of the protease activated receptor would similarly decrease the pain in a subject when those effectors are "activated" by the PAR activation. Decreasing activation of the protease activated receptor-2, as used herein, is intended to refer to one or both mechanisms, i.e. where the activation of the receptor is decreased and/or where the downstream effects of the receptor are decreased.

To elaborate further, activation of PAR-2 can be decreased by various methods, at the gene and protein and structural levels. In one embodiment, the levels are decreased by decreasing PAR-2 gene expression of the PAR-2 in the cells. This can be accomplished by exposing the cells to a compound which decreases PAR-2 gene expression of the PAR-2. The compound could be, for example, an antisense oligonucleotide targeted to the PAR-2 gene.

In a similar embodiment, the compound which decreases PAR-2 gene expression of the PAR-2 could be a ribozyme, which is a special category of antisense RNA molecule having a recognition sequence complementary to the mRNA encoding the PAR-2. A ribozyme not only complexes with a target sequence via complementary antisense sequences, but also catalyzes the hydrolysis, or cleavage, of the template mRNA molecule. The expression of the PAR-2 protein is therefore prevented.

Other methods for decreasing PAR-2 gene expression could also involve site-directed mutagenesis of the PAR-2 gene to prevent expression of the PAR-2, or various gene therapy techniques.

Levels, in particular activity, of PAR-2 in the cell can also be decreased by exposing the cells to an inhibitor of the PAR-2. Such inhibitors include chemical inhibitors or peptide inhibitors (which can be identified in accordance with the references cited above).

Levels of PAR-2 in the cell can also be decreased by exposing the cells to a compound which interferes with receptor formation by the PAR-2 (transmembrane structure).

Since the method of the subject invention is a method of decreasing pain, the subject can be human or animal.

The method is useful in an inflammatory condition. Examples of inflammatory conditions include regional inflammatory disorders, such as asthma (late phase), pancreatitis, inflammatory bowel disease (IBD), peritonitis, rheumatoid arthritis, osteoarthritis, myocardial infarction, ocular inflammatory states, and stroke. Examples of inflammatory conditions also include systemic inflammatory disorders, such as systemic inflammatory response syndrome (SIRS), cardiogenic shock, adult respiratory distress syndrome (ARDS), multiple-organ dysfunction (MOD), septic shock, and infant respiratory distress syndrome (IRDS).

The invention is also useful in non-inflammatory conditions which involve pain, examples of which are well known in the art.

In one embodiment, the invention employs oligonucleotides targeted to nucleic acids encoding protease activated receptor-2 (PAR-2). The relationship between an oligonucleotide and its complementary nucleic acid target to which it hybridizes is commonly referred to as "antisense". "Targeting" an oligonucleotide to a chosen nucleic acid target, in the context of this invention, is a multistep process. The process usually begins with identifying a nucleic acid sequence whose function is to be modulated. In the subject invention, this may be, for example, the cellular gene (or mRNA made from the gene) for PAR-2; i.e., the target is a nucleic acid encoding PAR-2, the PAR-2 gene, or mRNA expressed from the PAR-2 gene. The targeting process also includes determination of a site or sites within the nucleic acid sequence for the oligonucleotide interaction to occur such that the desired effect, modulation of gene expression, will result. Once the target site or sites have been identified, oligonucleotides are chosen which are sufficiently complementary to the target, i.e., hybridize sufficiently well and with sufficient specificity, to give the desired modulation.

"Hybridization", in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them. "Specifically hybridizable" and "complementary" are terms which are used to indicate a sufficient degree of complementarity such that stable and specific binding occurs between the DNA or RNA target and the oligonucleotide. It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

In various embodiments of this invention, oligonucleotides are provided which are targeted to mRNA encoding PAR-2. In accordance with this invention, persons of ordinary skill in the art will understand that mRNA includes not only the coding region which carries the information to encode a gene product using the three letter genetic code, including the translation start and stop codons, but also associated ribonucleotides which form a region known to such persons as the 5'-untranslated region, the 3'-untranslated region, the 5' cap region, intron regions and intron/exon or splice junction ribonucleotides. Thus, oligonucleotides may be formulated in accordance with this invention which are targeted wholly or in part to these associated ribonucleotides as well as to the coding ribonucleotides. The functions of mRNA to be interfered with include all vital functions such as translocation of the RNA to the site for protein translation, actual translation of protein from the RNA, splicing or maturation of the RNA and possibly even independent catalytic activity which may be engaged in by the RNA. The overall effect of such interference with the RNA function is to cause interference with PAR-2 gene expression.

In the context of this invention, the term "oligonucleotide" refers to an oligomer or polymer of nucleotide or nucleoside monomers consisting of naturally occurring bases, sugars and intersugar (backbone) linkages. The term "oligonucleotide" also includes oligomers comprising non-naturally occurring monomers, or portions thereof, which function similarly. Such modified or substituted oligonucleotides are often preferred over native forms because of properties such as, for example, enhanced cellular uptake and increased stability in the presence of nucleases.

The compounds and/or inhibitors used in the methods of the subject invention encompass any pharmaceutically acceptable salts, esters, or salts of such esters, or any other compound/inhibitor which, upon administration to an animal including a human, is capable of providing (directly or indirectly) the biologically active metabolite or residue thereof. Accordingly, for example, the disclosure is also drawn to prodrugs and pharmaceutically acceptable salts of the compounds and/or inhibitors used in the subject invention, pharmaceutically acceptable salts of such prodrugs, and other bioequivalents.

In regard to prodrugs, the compounds and/or inhibitors for use in the invention may additionally or alternatively be prepared to be delivered in a prodrug form. The term prodrug indicates a therapeutic agent that is prepared in an inactive form that is converted to an active form (i.e., drug) within the body or cells thereof by the action of endogenous enzymes or other chemicals and/or conditions.

In regard to pharmaceutically acceptable salts, the term pharmaceutically acceptable salts refers to physiologically and pharmaceutically acceptable salts of the compounds and/or inhibitors used in the subject invention: i.e., salts that retain the desired biological activity of the parent compound and do not impart undesired toxicological effects thereto.

The oligonucleotides used in the method of the subject invention preferably are from about 8 to about 50 nucleotides in length. In the context of this invention it is understood that this encompasses non-naturally occurring oligomers, preferably having 8 to 50 monomers.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the skill of the art. It is also well known to use similar techniques to prepare other oligonucleotides such as the phosphorothioates and alkylated derivatives. It is also well known to use similar techniques and commercially available modified amidites and controlled-pore glass (CPG) products such as biotin, fluorescein, acridine or psoralen-modified amidites and/or CPG (available from Glen Research, Sterling Va.) to synthesize fluorescently labeled, biotinylated or other modified oligonucleotides such as cholesterol-modified oligonucleotides.

In the context of this invention, to "expose" cells (including the cells of tissues) to a compound and/or inhibitor means to add the compound and/or inhibitor, usually in a liquid carrier, to a cell suspension or tissue sample, either in vitro or ex vivo, or to administer the compounds and/or inhibitor to cells or tissues within an animal (including a human) subject.

For therapeutics, methods of decreasing pain are provided. The formulation of therapeutic compositions and their subsequent administration is believed to be within the skill in the art. In general, for therapeutics, a patient suspected of needing such therapy is given a compound and/or inhibitor in accordance with the invention, commonly in a pharmaceutically acceptable carrier, in amounts and for periods which will vary depending upon the nature of the particular disease, its severity and the patient's overall condition. The pharmaceutical compositions may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip or infusion, subcutaneous, intraperitoneal or intramuscular injection, pulmonary administration, e.g., by inhalation or insufflation, or intrathecal or intraventricular administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for parenteral, intrathecal or intraventricular administration may include sterile aqueous solutions which may also contain buffers, diluents and other suitable additives.

In addition to such pharmaceutical carriers, cationic lipids may be included in the formulation to facilitate oligonucleotide uptake. One such composition shown to facilitate uptake is Lipofectin (BRL, Bethesda Md.).

Dosing is dependent on severity and responsiveness of the condition to be treated, with course of treatment lasting from several days to several months or until a cure is effected or a diminution of disease state is achieved. Optimal dosing schedules can be calculated from measurements of drug accumulation in the body. Persons of ordinary skill can easily determine optimum dosages, dosing methodologies and repetition rates. Optimum dosages may vary depending on the relative potency of individual compounds and/or inhibitors, and can generally be calculated based on $IC_{50}$'s or $EC_{50}$'s in in vitro and in vivo animal studies. For example, given the molecular weight of compound (derived from oligonucleotide sequence and/or chemical structure) and an effective dose such as an $IC_{50}$, for example (derived experimentally), a dose in mg/kg is routinely calculated.

The nucleic acid and amino acid sequences of various protease activated receptor-2 genes are known and readily available from GenBank and described in the literature (see above discussion).

Given these sequences, one can design appropriate antisense molecules for use in the subject invention. Furthermore, by expressing the PAR-2 in a host cell, one can screen for suitable compounds and/or inhibitors for use in the subject invention. The activation of the encoded receptor can be assayed according to methods known in the art.

Drugs, such as peptide drugs, which inhibit the PAR-2 or which interfere with formation of the transmembrane receptor PAR-2 can be made using various methods known in the art. Initially, a monoclonal antibody can be prepared which specifically hybridizes to the PAR-2, thereby interfering with activity and/or receptor formation.

The monoclonal antibodies can be produced by hybridomas. A hybridoma is an immortalized cell line which is capable of secreting a specific monoclonal antibody.

In general, techniques for preparing polyclonal and monoclonal antibodies as well as hybridomas capable of producing the desired antibody are well known in the art (see Campbell, A. M., "Monoclonal Antibody Technology: Laboratory Techniques in Biochemistry and Molecular Biology", Elsevier Science Publishers, Amsterdam, The Netherlands (1984); St. Groth, et al., J Immunol Methods 35:1-21 (1980)). Any animal (mouse, rabbit, etc.) which is known to produce antibodies can be immunized with the PAR-2 (or an antigenic fragment thereof). Methods for immunization are well known in the art. Such methods include subcutaneous or intraperitoneal injection of the PAR-2. One skilled in the art will recognize that the amount of the PAR-2 used for immunization will vary based on the animal which is immunized, the antigenicity of the PAR-2, and the site of injection.

The PAR-2 which is used as an immunogen may be modified or administered in an adjuvant in order to increase the PAR-2's antigenicity. Methods of increasing the antigenicity of a protein are well known in the art and include, but are not limited to, coupling the antigen with a heterologous protein (such as a globulin or beta-galactosidase) or through the inclusion of an adjuvant during immunization.

For monoclonal antibodies, spleen cells from the immunized animals are removed, fused with myeloma cells, such as SP2/O-Ag 15 myeloma cells, and allowed to become monoclonal antibody producing hybridoma cells.

Any one of a number of methods well known in the art can be used to identify the hybridoma cell which produces an antibody with the desired characteristics. These include screening the hybridomas with an ELISA assay, western blot analysis, or radioimmunoassay (Lutz, et al., Exp Cell Res 175:109-124 (1988)).

Hybridomas secreting the desired antibodies are cloned and the class and subclass are determined using procedures known in the art (Campbell, A. M., "Monoclonal Antibody Technology Laboratory Techniques in Biochemistry and Molecular Biology", Elsevier Science Publishers, Amsterdam, The Netherlands (1984)).

For polyclonal antibodies, antibody containing antisera is isolated from the immunized animal and is screened for the presence of antibodies with the desired specificity using one of the above-described procedures.

Once a monoclonal antibody which specifically hydridizes to the PAR-2 is identified, the monoclonal (which is itself a compound or inhibitor which can be used in the subject invention) can be used to identify peptides capable of mimicking the inhibitory activity of the monoclonal antibody. One such method utilizes the development of epitope libraries and biopanning of bacteriophage libraries. Briefly, attempts to define the binding sites for various monoclonal antibodies have led to the development of epitope libraries. Parmley and Smith developed a bacteriophage expression vector that could display foreign epitopes on its surface (Parmley, S. F. & Smith, G. P., Gene 73:305-318 (1988)). This vector could be used to construct large collections of bacteriophage which could include virtually all possible sequences of a short (e.g. six-amino-acid) peptide. They also developed biopanning, which is a method for affinity-purifying phage displaying foreign epitopes using a specific antibody (see Parmley, S. F. & Smith, G. P., Gene 73:305-318 (1988); Cwirla, S. E., et al., Proc Natl Acad Sci USA 87:6378-6382 (1990); Scott, J. K. & Smith, G. P., Science 249:386-390 (1990); Christian, R. B., et al., J Mol Biol 227:711-718 (1992); Smith, G. P. & Scott, J. K., Methods in Enzymology 217:228-257 (1993)).

After the development of epitope libraries, Smith et al. then suggested that it should be possible to use the bacteriophage expression vector and biopanning technique of Parmley and Smith to identify epitopes from all possible sequences of a given length. This led to the idea of identifying peptide ligands for antibodies by biopanning epitope libraries, which could then be used in vaccine design, epitope mapping, the identification of genes, and many other applications (Parmley, S. F. & Smith, G. P., Gene 73:305-318 (1988); Scott, J. K., Trends in Biochem Sci 17:241-245 (1992)).

Using epitope libraries and biopanning, researchers searching for epitope sequences found instead peptide sequences which mimicked the epitope, i.e., sequences which did not identify a continuous linear native sequence or necessarily occur at all within a natural protein sequence. These mimicking peptides are called mimotopes. In this manner, mimotopes of various binding sites/proteins have been found.

The sequences of these mimotopes, by definition, do not identify a continuous linear native sequence or necessarily occur in any way in a naturally-occurring molecule, i.e. a naturally occurring protein. The sequences of the mimotopes merely form a peptide which functionally mimics a binding site on a naturally-occurring protein.

Many of these mimotopes are short peptides. The availability of short peptides which can be readily synthesized in large amounts and which can mimic naturally-occurring sequences (i.e. binding sites) offers great potential application.

Using this technique, mimotopes to a monoclonal antibody that recognizes PAR-2 can be identified. The sequences of these mimotopes represent short peptides which can then be used in various ways, for example as peptide drugs that bind to PAR-2 and decrease the activity of PAR-2. Once the sequence of the mimotope is determined, the peptide drugs can be chemically synthesized.

The peptides for use in the subject invention can contain any naturally-occurring or non-naturally-occurring amino acids, including the D-form of the amino acids, amino acid derivatives and amino acid mimics, so long as the desired function and activity of the peptide is maintained. The choice of including an (L)- or a (D)-amino acid in the peptide depends, in part, on the desired characteristics of the peptide. For example, the incorporation of one or more (D)-amino acids can confer increased stability on a peptide and can allow a peptide to remain active in the body for an extended period of time. The incorporation of one or more (D)-amino acids can also increase or decrease the pharmacological activity of a peptide.

The peptide may also be cyclized, since cyclization may provide the peptide with superior properties over their linear counterparts.

Modifications to the peptide backbone and peptide bonds thereof are encompassed within the scope of amino acid mimic or mimetic. Such modifications can be made to the amino acid, derivative thereof, non-amino acid moiety or the peptide either before or after the amino acid, derivative thereof or non-amino acid moiety is incorporated into the peptide. What is critical is that such modifications mimic the peptide backbone and bonds which make up the same and have substantially the same spacial arrangement and distance as is typical for traditional peptide bonds and backbones. An example of one such modification is the reduction of the carbonyl(s) of the amide peptide backbone to an amine. A number of reagents are available and well known for the reduction of amides to amines such as those disclosed in Wann et al., JOC 46:257 (1981) and Raucher et al., Tetrahedron Lett 21:14061 (1980). An amino acid mimic is, therefore, an organic molecule that retains the similar amino acid pharmacophore groups as are present in the corresponding amino acid and which exhibits substantially the same spatial arrangement between functional groups.

The substitution of amino acids by non-naturally occurring amino acids and amino acid mimics as described above can enhance the overall activity or properties of an individual peptide thereof based on the modifications to the backbone or side chain functionalities. For example, these types of alterations can enhance the peptide's stability to enzymatic breakdown and increase biological activity. Modifications to the peptide backbone similarly can add stability and enhance activity.

One skilled in the art, using the identified sequences can easily synthesize the peptides for use in the invention. Standard procedures for preparing synthetic peptides are well known in the art. The novel peptides can be synthesized using: the solid phase peptide synthesis (SPPS) method of Merrifield, J Am Chem Soc 85:2149 (1964) or modifications of SPPS; or, the peptides can be synthesized using standard solution methods well known in the art (see, for example, Bodanzsky, "Principles of Peptide Synthesis", 2d Ed., Springer-Verlag (1993)). Alternatively, simultaneous multiple peptide synthesis (SMPS) techniques well known in the art can be used. Peptides prepared by the method of Merrifield can be synthesized using an automated peptide synthesizer such as the Applied Biosystems 431A-01 Peptide Synthesizer (Mountain View, Calif.) or using the manual peptide synthesis technique described by Houghten, Proc Natl Acad Sci USA 82:5131 (1985).

The subject invention is based on the discovery that links activation of the protease activated receptor-2 to nociception (pain perception). This teaches that PAR-2 antagonists can be used in the treatment of painful conditions in general (as antinociceptive agents). Due to its role in modulating nociceptive neuronal function, the protease activated receptor-2 (PAR-2) represents a useful target for development of analgesic drugs.

In the results which follow, it is shown that activated proteases can have direct effects on sensory neurons, mediated by specific receptors. PAR-1 and PAR-2 are present in rat DRGs (Young et al. 2000). The presence of one of these receptors, PAR-2, in sensory neurons is first confirmed by finding evidence of mRNA and protein expression in adult rat thoracic DRGs. The functional implications of PAR-2 expression are then examined by assessing the response of primary neuronal cultures to trypsin and AcPep. Both agonists increased intracellular $Ca^{2+}$ confirming previously reported findings that a functional PAR 2 receptor is present in adult rat DRGs (Steinhoff et al. 2000). Trypsin stimulates both PAR-1 and PAR-2 and therefore an increase in intracellular $Ca^{2+}$ can be caused by activation of the two different receptors. However, the AcPep SEQ ID NO:3: SLIGRL only activates PAR-2 and does not activate PAR-1 (Blackhart et al. 1996). Therefore the increased intracellular $Ca^{2+}$ response to AcPep reflects specific PAR-2 mediated activation.

Stimulus evoked neuropeptide release is a key measure of sensory neuron function. Adult DRG neurons can be sensitized in vitro by a specific PAR-2 agonist, as measured by enhancement of stimulus provoked CGRP release. AcPep alone at a concentration of 10 µM does not induce CGRP release; however, AcPep significantly enhances both Capsaicin and KCl-evoked CGRP release in primary neuronal cultures. Exposing the neurons to AcPep 10 µM augmented the Capsaicin and KCl-evoked CGRP release almost 2-fold and 1.5-fold (multiple of the basal release for each individual release experiment), respectively. This shows that adult rat DRG neurons can be sensitized in vitro through a PAR-2 specific mechanism and supports that PAR 2 plays a role in nociception through sensitization of afferent nerves.

In vivo, Steinhoff et al. (2000) have demonstrated that subcutaneous injection of 500 µg AcPep into the rat paw results in the release of CGRP and Substance P from peripheral afferent nerve endings. The results below show the determination of whether such activation could also lead to the release of these neurotransmitters centrally and enhance the nociceptive response. To investigate this, AcPep alone and AcPep followed by Capsaicin were injected into the pancreatic duct of adult rats and c-FOS expression in the superficial dorsal horn laminae was studied 2.5 hours later. C-FOS expression functions as an indirect marker of nociceptive transmission and has been widely accepted as a nociceptive marker at the spinal cord level (Chapman and Besson 1997; Hunt et al. 1987). Intraductal injection of AcPep 10 µM significantly increased the expression of c-FOS in the corresponding spinal segments T8-T10 when compared to control rats. This increase in expression of c-FOS decreased in a bell-shaped fashion in the nearby thoracic segments, serving as an internal control for a specific effect of AcPep through PAR-2 positive pancreatic afferent neurons. The injection of CoPep plus Capsaicin was as strong a stimulant as AcPep alone. AcPep enhanced Capsaicin-evoked c-FOS expression as compared to controls.

There was no evidence of pancreatitis and there was no difference in the histology of the individual treatment groups that could potentially account for a difference in c-FOS expression. These observations show that pancreatic sensory neurons can mediate nociception through a PAR-2 mediated mechanism that is independent of the presence of inflammation.

AcPep treatment had no effect on basal CGRP release from cultured DRG neurons: when primary cultures of DRG neurons were treated for 10 minutes with AcPep, there was no change in CGRP content in the release buffer as compared to controls. However, AcPep infused into the pancreatic duct does increase c-FOS expression in spinal cord neurons as compared to controls. From these data it can be concluded that AcPep infusion into the pancreas increased c-FOS expression in the thoracic spinal cord segments examined. These findings are consistent with AcPep activation of pancreatic sensory afferent neurons thereby producing greater input into the spinal cord and greater c-FOS expression. These findings are consistent with Bunnett's experiments showing AcPep-induced increases in CGRP release from spinal cord sections and AcPep-induced increases in plasma extravasation suggesting that in "intact" preparations as opposed to dissociated neurons in culture, AcPep can elicit neuropeptide release from sensory nerve endings.

The results presented herein show a new role of PAR-2 as an important mediator in nociceptive signaling and provide evidence for a novel link between inflammation and pain (FIG. 7).

Materials and Methods

Animals. Adult male rats (Sprague-Dawley, 200-250 g) were used in all experiments. Experimental protocols involving animals were approved by the UTMB Institutional Animal Care and Use Committee (IACUC).

RT-PCR. Total RNA was made from the dorsal root ganglia (DRG) of normal male Sprague-Dawley rats, using the Ultraspect™ RNA isolation system (Biotex Laboratories, Inc., Houston, Tex.) and treated with DNAseI. RT-PCR (ProSTAR Ultra HF RT-PCR System, Stratagene) was performed using PAR 2-specific primers (SEQ ID NO:1: 5'-TCA GTA GGA GGT TTT AAC AC-3' and SEQ ID NO:2: 5'-ATG CGA AGT CTC AGC CTG GC-3') as follows: initial denaturation 95° C. for 1 min (1 cycle), 95° C. for 1 min, 56° C. for 1 min, 68° C. for 15 min, 68° C. final extension for 10 minutes. The fragments were purified from a low melt agarose gel and were ligated into a plasmid vector, pGEM 5Z(f)+ (Promega). The identity of the PCR product was confirmed by sequence analysis using an automated ABI sequencer.

Confocal microscopy. Primary neuronal cultures were fixed in 100% Methanol for 10 minutes at −20° C. and incubated for 20 minutes with PBS containing 0.3% Triton X-100 and 5% normal donkey serum. Slides were incubated overnight at 4° C. with primary antisera diluted in PBS containing 5% normal donkey serum, rinsed in PBS at room temperature and were incubated with species-specific secondary antibody labeled with fluorophores for 1 hr at room temperature. Slides were washed in PBS, rinsed in $dH_2O$ and were mounted with Fluor Save (Calbiochem, La Jolla, Calif.). Serial, confocal optical sections of a z-series were obtained with a video-rate confocal laser scanning microscope.

Antisera. A goat polyclonal antibody raised against the amino acid terminus of the PAR-2 receptor was used at a dilution of 1:200 (Santa Cruz Biotechnology, Inc, Santa Cruz, Calif.). Donkey-anti-goat (Alexa 594) secondary antiserum was used at a dilution of 1:200.

Cell Culture. Primary cultures of rat DRG neurons were prepared from male adult Sprague Dawley rats (200-250 gm). Following enzymatic treatment and dissociation, neurons were spun through a percoll cushion (Hofbauer et al. 1998) and were plated at a density of 10,000-20,000 neurons/well of a 48 well tissue culture plate. Cultures were maintained in DME+10% FCS supplemented with penicillin/streptomycin, 150 μM uridine and 50 μM 5-fluoro-2-deoxyuridine (Nguyen et al. 1999). NGF (murine, recombinant, 2.5S; Promega, Madison, Wis.) was used at 50 ng/ml. Neurons were treated for five days before release experiments or Calcium-imaging studies were performed.

CGRP release assay. Immunoreactive calcitonin gene-related peptide (IR-CGRP) release from DRG cultures was performed as described by Hingtgen et al. (1995). Briefly, neuron cultures were washed with Release Buffer (RB) (25 mM Hepes, pH 7.4, 135 mM NaCl, 3.5 mM KCl, 2.5 mM $CaCl_2$, 1 mM $MgCl_2$, 3.3 mM Glucose, 0.1% BSA, 1 μM phosphoamidon), and were incubated for 10 min at 37° C. in RB plus 0.1% ethanol (Capsaicin vehicle) to measure basal CGRP release. Fresh RB containing the appropriate concentration of activating peptide (AcPep) or control peptide (CoPep) was added for an additional 10 minutes. Peptide treatment was followed by a 10 minute incubation with an appropriate dose of Capsaicin or KCl. IR-CGRP released by neurons was measured by ELISA. Activating peptide and control peptide were prepared by standard solid phase synthesis procedures by the UTMB Core Protein Facility.

CGRP Quantification. CGRP was quantified in a standard sandwich ELISA. In brief, 96-well "U" bottom microtiter ELISA plates (Dynex, Chantilly, Va.) were coated with affinity purified polyclonal rabbit antibody to rat CGRP (Peninsula Labs, Belmont, Calif.) at 3 μg/ml in 0.125M borate buffered saline (pH 8.1) (100 μl/well). The plates were incubated overnight at 37° C. The next day, the plates were washed three times with saline containing 0.05% Tween-20. Purified rat CGRP (Peninsula Labs) was used at a previously standardized concentration range of 25-1 ng/ml in a four-fold dilution to generate a standard curve. An equal volume of the sample was added in duplicate to a seventy-five μl/well of Tween-PBS (pH 7.1) and the plates were incubated for two hours on a shaker at room temperature. The plates were washed 3 times with Tween-PBS and 100 μl/well (0.2 mg/ml; 1:500 dilution) of in-house biotinylated, rabbit anti rat CGRP IgG (Peninsula Labs) was applied and incubated for two hours at room temperature. After three washes 150 μl of 1:1000 diluted streptavidine-horseradish peroxidase conjugate (Zymed, San Fransisco, Calif.) was added to each well and the plates were incubated for 90 min at room temperature. One-hundred-fifty μl/well of the substrate ortho-phenylene diamine dihydrochloride (Sigma Chemicals, St. Louis, Mo.) 0.4 mg/ml in citrate buffer (pH 4.9) was added after plates were washed three more times. Forty μl/100 ml of 30% $H_2O_2$ was added fresh to the citrate buffer just before adding to the wells to activate the coloring reaction. The reaction was stopped with 5N $H_2SO_4$ (50 μl/well) and the plates were read at 490 nM in an automated ELISA reader (Bio-Tek Instruments, Inc., Winooski, VE). The OD values were plotted against the CGRP standard curve and CGRP immunoreactivity was quantified using the appropriate formula and expressed as nanogram/ml.

Intraductal (pancreatic duct) injection. To administer the necessary peptides directly into the rat pancreatic duct we followed a modified protocol, previously described by Kim et al. (1996). In brief, rats were anesthetized i.p. with nembutal sodium (Abbot Laboratories, Chicago, Ill.) (50 mg/kg body weight). The peritoneum was incised to expose the duodenum and the duodenal loop was pulled out. The pancreatic duct entering the duodenum was identified under dissecting microscope and a small niche was made into the duct with a 30-gauge needle. A polyethylene 10 tubing (0.61 mm outer diameter) (Becton Dickinson and Company, Franklin Lakes, N.J.) was guided into the duct and tied to secure its position. The common bile duct was ligated close to the liver to prevent entry of the injected substance into the liver. Similarly the duct was ligated near its entry into the duodenum. The position of the tube into the pancreatic duct was confirmed by freely flowing bile through the tubing. Five-hundred μl per rat of 100 μM AcPep or CoPep were injected through a syringe connected to the tubing. Thirty minutes later Capsaicin 0.5 mg/kg (total volume 500 μl) or vehicle (1×PBS, 10% ETOH, 1% Tween) was injected to half of the AcPep or CoPep injected rats. Three rats were included in each treatment group (n=3 for number of experiments). The tubing was carefully removed and bile flow from the liver into the duodenum was re-established. The abdominal cavity was closed with sutures. Rats were sacrificed 2.5 hrs after the initial injection.

C-fos staining. Rats were anesthetized with sodium pentobarbital (50 mg/kg i.p.) and perfused with 200 mls PBS followed by 500 mls ice-cold freshly prepared 4% paraformaldehyde in PBS. Spinal cord (level T5-T13) was removed, post-fixed in 4% paraformaldehyde for 18 hrs at 4° C. and placed in PBS (pH 7.4) containing 30% sucrose for 24 hrs at 4° C. Frozen sections (40 μm) were cut on a cryostat and stored as floating sections in PBS at 4° C. Every third section was stained for c-fos with a rabbit polyclonal serum, 1:1000 dilution, (c-fos, Ab-5, Oncogene Research Products) utilizing manufacturer's protocol. Antibody staining was visualized using a biotinylated secondary antisera and Vectastain ABC peroxidase kit with DAB as substrate. Sections were mounted on Superfrost Plus slides (VWR Scientific, West Chester, Pa.) and dehydrated. The number of c-FOS immunoreactive (IR) neurons were counted in 10 randomly chosen sections per segment under brightfield illumination and then averaged.

Pancreatic histology. Fresh specimens of rat pancreas were fixed in 10% formaldehyde (Sigma) in phosphate-buffered saline (PBS) pH 7.4 containing 1 mM $MgCl_2$ at 4° C. overnight. Sections from paraffin-embedded specimens were stained with hematoxyline and eosin and observed under a light microscope (BX60, Olympus, Tokyo, Japan). Evaluation of the pathologic changes on sections was based on the scales described by Tito et al. (1993). A pathologist blinded for the different treatment groups evaluated all sections.

Statistics. Release data are presented as the mean± standard error of the mean (SEM) of wells from three separate experiments. To compare the effects of activating peptide and control peptide on subsequent evoked release, an overall test based on the analysis of variance was performed (ANOVA). If this test indicated that a difference existed, individual means were compared using the Bonferroni's multiple comparison test. Intraductal injection studies were analyzed using a repeated measure ANOVA and individual means were compared using a Newman-Keuls multiple comparison test. Significance levels were set at p<0.05.

EXAMPLE I

PAR 2 is Expressed in Adult Rat Thoracic DRG Neurons

A previous report has demonstrated PAR-2 expression in neurons from adult rat lumbar dorsal root ganglia (Steinhoff et al. 2000). The presence of this receptor on adult rat thoracic DRG was confirmed by amplifying the entire coding region of the PAR-2 gene by RT-PCR from total RNA, using PAR-2 specific primers. PAR-2 immunoreactivity (IR) was also detected in cultured primary neurons using a PAR-2 specific antibody. PAR-2 IR was noted both at the plasma membrane and in the cytoplasm of the neuronal soma. Thus, PAR-2 is expressed in adult rat thoracic DRG neurons.

EXAMPLE II

The PAR-2 Agonist Activating Peptide (AcPep) Increases Capsaicin and KCl-Evoked CGRP Release in Cultured Neurons To determine whether PAR-2 activation could enhance a stimulus-evoked release of CGRP, the effect of treatment with the PAR-2 activating peptide (AcPep) (SEQ ID NO:3: SLI-GRL) 10 minutes prior to and throughout a 10 minute incubation with KCl (70 mM) or Capsaicin (50 nM) was examined in cultured NGF-treated adult rat thoracic DRG neurons (FIGS. 1-4). The reverse peptide sequence of AcPep (SEQ ID NO:4: RLGILS-amide) was used as a control peptide (CoPep). Treatment with AcPep (10 μM) by itself did not significantly increase CGRP release during a 10 minute incubation period. Pre-treatment with AcPep 10 μM for 10 minutes caused a significantly higher increase in subsequent KCl evoked IR-CGRP release in contrast to CoPep treatment (p<0.01). Similarly, pretreatment of neurons with AcPep caused a significant increase in Capsaicin-evoked CGRP release as compared to CoPep (p<0.001). The results indicate that the PAR 2 specific agonist AcPep can sensitize adult rat thoracic DRG neurons in vitro. AcPep did not itself induce CGRP release.

EXAMPLE III

Activating Peptide Increases c-FOS Expression in Pancreatic Spinal Segments

Figure 5:
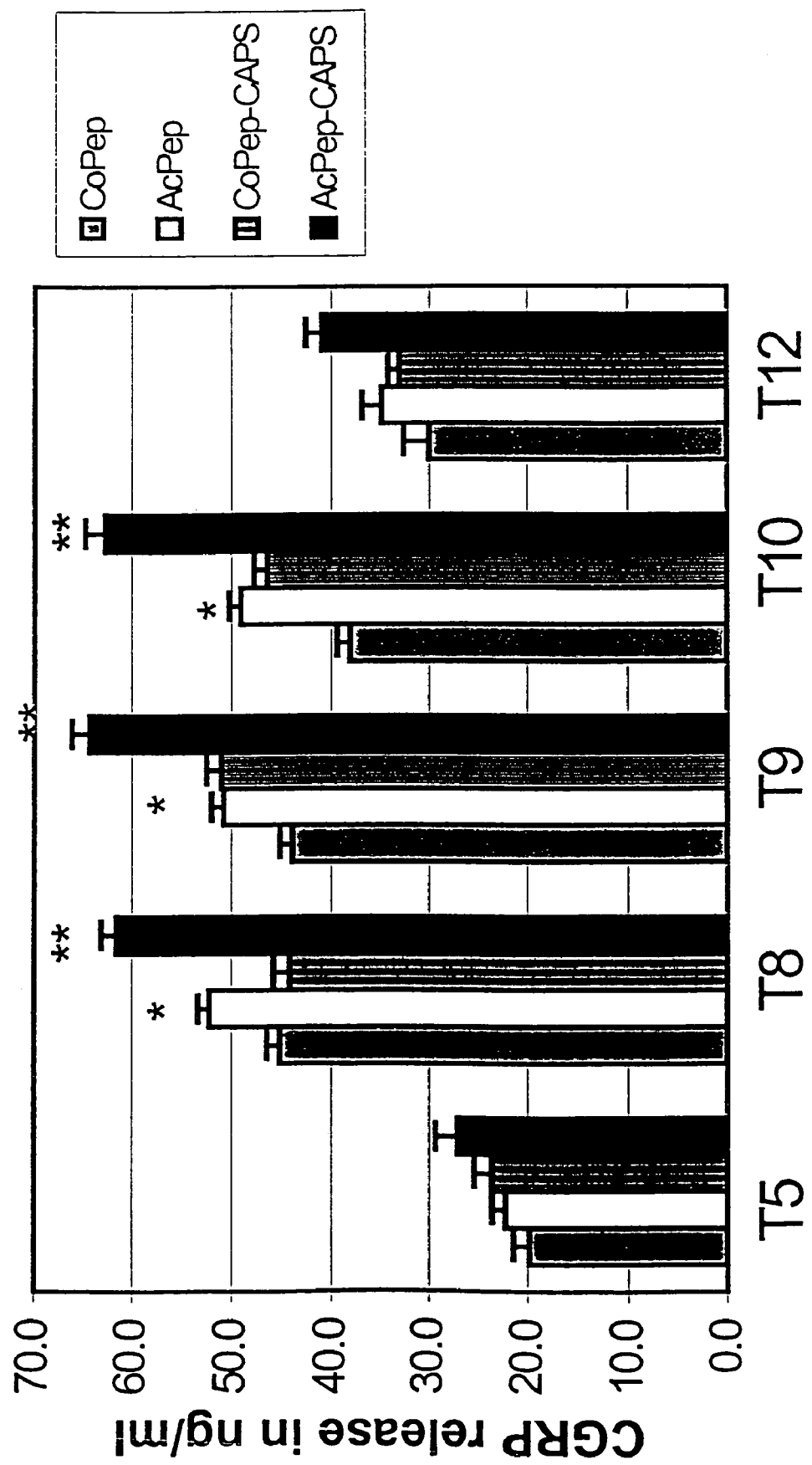
FIG. 5 is a histogram showing the distribution of c-FOS-IR nuclei in rat spinal cord segments following infusion of AcPep alone, CoPep alone, AcPep followed by Capsaicin or CoPep followed by Capsaicin into the pancreatic duct. Infusion of AcPep 100 μM alone into the pancreatic duct produced more c-FOS IR neurons in segments T8-T10 compared to CoPep (*p<0.01 vs CoPep). When infusion of AcPep or CoPep was followed by infusion of Capsaicin (0.5 mg/kg in 0.5 mls) more c-FOS was observed following pre-treatments with AcPep (**p<0.001 vs CoPep/Caps). T5 and T12 are control segments to demonstrate that the effect of AcPep injection is specific for pancreatic segments T8-T10.
Figure 6:
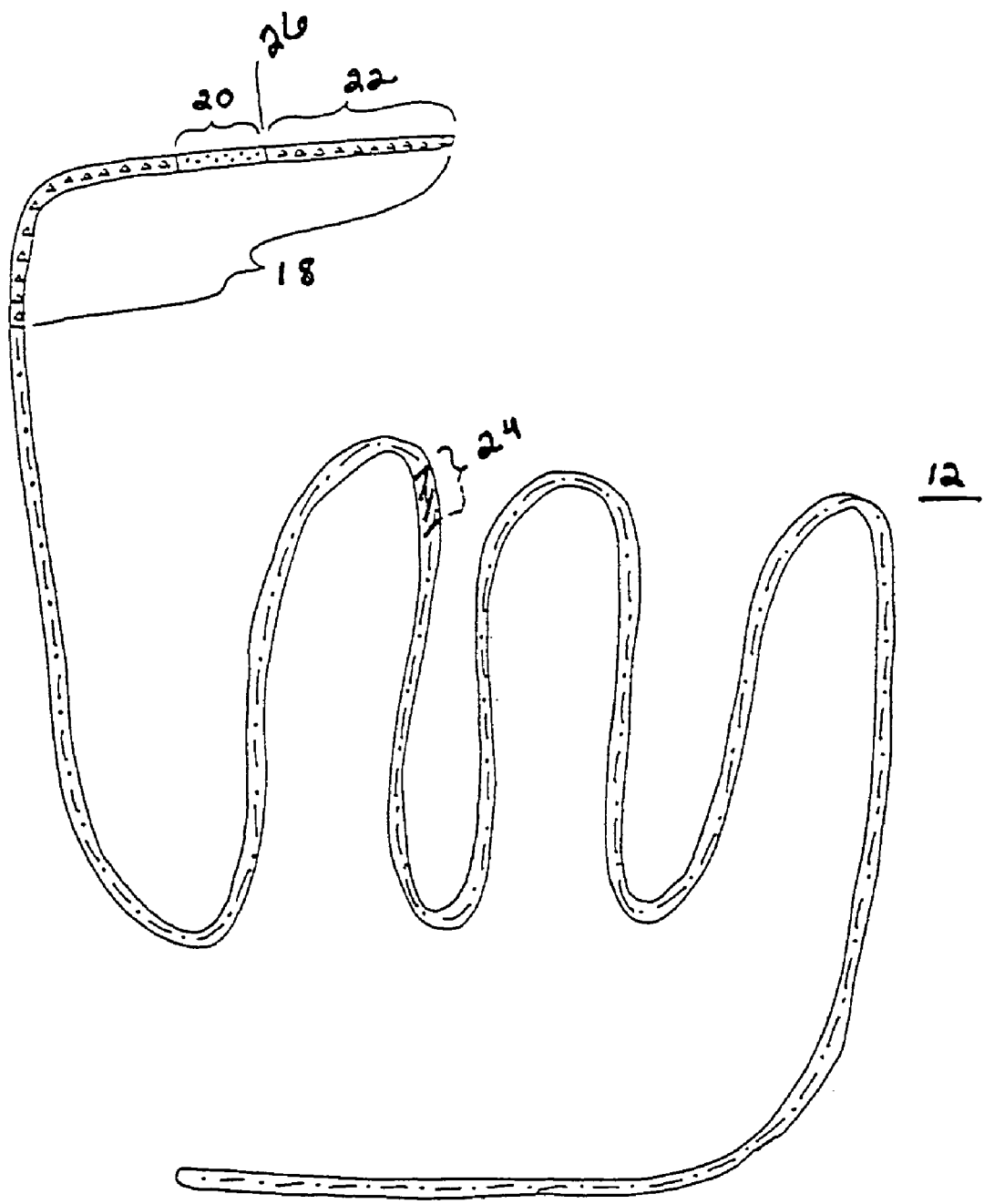
FIG. 6 is a diagram of the general structure of protease activated receptors.

To evaluate the role of PAR-2 activation in nociception, the effect of pancreatic intraductal AcPep injections on c-FOS expression and on Capsaicin-evoked c-FOS expression was studied in vivo. Segments receiving input from the pancreas (T8-T10) were studied; spinal segments T5 and T12 served as internal controls to assure that the effects noted on c-FOS expression were specific to the pancreas (FIG. 5). All animals were injected with AcPep 100 μM or CoPep 100 μM. Half of the animals received a second injection of Capsaicin or vehicle thirty minutes after the first injection. Animals were sacrificed 2.5 hours after the initial injection. Infusion of AcPep alone into the pancreatic duct produced more c-FOS IR neurons in segments T8-T10 compared to CoPep injection alone (p>0.05). When infusion of AcPep or CoPep was followed by infusion of Capsaicin more c-FOS was observed following pre-treatments with AcPep (p<0.001). No significant differences in c-FOS expression were observed between treatment groups in segments T5 or T12. Thus, a PAR-2 agonist infused into the pancreatic duct sensitized pancreatic afferent fibers in a manner that is independent of the presence of inflammation.

EXAMPLE IV

Pancreatic Histology

The pancreas was obtained for histology and scored by a pathologist blinded for the different treatment groups. A histological scoring system was used (Tito et al. 1993). There was no evidence of pancreatitis on histology in any of the animals and there were no histological differences found amongst the different treatment groups (overall inflammatory score 0.5 for each group; p=NS).

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

LIST OF REFERENCES

Andrade-Gordon et al., Proc Natl Acad Sci USA 96(22): 12257-12262 (1999).
Al-Ani et al., J Pharmacol Exp Ther 290(2):753-760 (1999).
Blackhart et al., J Biol Chem 271:16466-16471 (1996).
Bohm et al., Biochem J 314:1009-1016 (1996).
Chapman and Besson, "The Pharmacology of Pain: Handbook of Experimental Pharmacology", pp. 235-279 (1997).
Cocks and Moffat, TIPS 21:103-108 (2000).
Delree et al., J Neurosci Res 23:198-206 (1989).
Dery et al., Am J Physiol 274:C1429-C1452 (1998).
Dray, Br J Anaesth 751:125-131 (1995).
Hintgen et al., J Neurosci 15:5411-5419 (1995).
Hofbauer et al., Am J Physiol 275:G352-G362 (1998).
Hollenberg et al., Can J Physiol Pharmacol 75:832-841 (1997).
Hunt et al., Nature 328:632-634 (1987).
Ishihara et al., Nature, 386:502-506 (1997).
Kahn et al., Mol Med 2(3):349-357 (1996).
Kahn et al., Nature 394:690-694 (1998).
Kawabata et al., J Pharmacol Exp Ther 288(1):358-370 (1999).
Kim et al., Int J Pancreatology 20(3):205-211 (1996).
Lerner et al., J Biol Chem 271(24):13943-13947 (1996).
Nguyen et al., J Clin Inv 103(2):261-269 (1999).
Nystedt et al., Proc Natl Acad Sci USA 91:9208-9212 (1994).
Nystedt et al., Eur J Biochem 232:84-89 (1995).
Nystedt et al., J Biol Chem 271:14910-14915 (1996).
Steinhoff et al., Nature Medicine 6(2):151-158 (2000).
Tito et al., Am J Surg 165:690-696 (1993).
Vu et al., Cell 64:1057-1068 (1991).
Xu et al., Proc Natl Acad Sci USA 95:6642-6646 (1998).
Young et al., Gastroenterology 118:A2013 (2000).

What is claimed is:

1. A method of identifying an antinociceptive compound, comprising the steps of:

contacting neuronal cells containing protease activated receptor-2 (PAR-2) with a PAR-2 activator compound;

measuring a level of activated PAR-2 in the presence and absence of the PAR-2 activator compound: wherein an increase in the level of activated PAR-2 in the presence of the PAR-2 activator compound compared to a level in the absence of the PAR-2 activator compound indicates that the neuronal cells contain activated PAR-2;

contacting the cells with and without activated PAR-2 with a stimulator effective to induce expression of a nociceptor;

measuring a level of the nociceptor in the presence and absence of the nociceptor stimulator wherein an increase in the level of the nociceptor in the presence of activated PAR-2 compared to a level in the absence of activated PAR-2 indicates that activated PAR-2 stimulates expression of the nociceptor;

contacting the cells with stimulated nociceptor expression with a candidate compound; and measuring an expression level of the nociceptor in the presence and absence of the candidate compound; wherein a decrease in the stimulated nociceptor expression level in the presence of the candidate compound compared to the stimulated nociceptor expression level in the absence of the candidate compound indicates that said candidate compound is an antinociceptive compound.

2. The method of claim 1, wherein the nociceptor is calcitonin-gene related peptide (CGRP) or Fos gene.

* * * * *

SEQUENCE LISTING

<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: PAR-2
      specific PCR primer

<400> SEQUENCE: 1
tcagtaggag gttttaacac                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: PAR-2
      specific PCR primer

<400> SEQUENCE: 2
atgcgaagtc tcagcctggc                                              20

<210> SEQ ID NO 3
<211> LENGTH: 6
<212> TYPE: PRT
<213> ORGANISM: Rattus sp.
<220> FEATURE:
<221> NAME/KEY: PEPTIDE
<222> LOCATION: (1)..(6)
<223> OTHER INFORMATION: PAR-2 activating peptide

<400> SEQUENCE: 3

Ser Leu Ile Gly Arg Leu
 1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: control
      peptide

<400> SEQUENCE: 4

Arg Leu Gly Ile Leu Ser
 1               5

<210> SEQ ID NO 5
<211> LENGTH: 6
<212> TYPE: PRT
<213> ORGANISM: Homo sapiens
<220> FEATURE:
<221> NAME/KEY: PEPTIDE
<222> LOCATION: (1)..(6)
<223> OTHER INFORMATION: Thrombin activating peptide

<400> SEQUENCE: 5

Ser Phe Leu Leu Arg Asn
 1               5

<210> SEQ ID NO 6
<211> LENGTH: 6
<212> TYPE: PRT
<213> ORGANISM: Homo sapiens

```
<220> FEATURE:
<221> NAME/KEY: PEPTIDE
<222> LOCATION: (1)..(6)
<223> OTHER INFORMATION: PAR-2 activating peptide

<400> SEQUENCE: 6

Ser Leu Ile Gly Lys Val
 1               5
```